United States Patent [19]

McGary, Jr. et al.

[11] 4,434,126
[45] Feb. 28, 1984

[54] POWDER COATING PROCESS FOR FORMING SOFT FLEXIBLE POLYURETHANE FILM

[75] Inventors: Charles W. McGary, Jr., Centerville; Vincent J. Pascarella, Dayton; Robert A. Taller; Delmer R. Rhodes, both of Centerville; Paul E. Anglin, Dayton; Charles W. Daugherty, Xenia, all of Ohio

[73] Assignee: Warner-Lambert Company, Morris Plains, N.J.

[21] Appl. No.: 357,915

[22] Filed: Mar. 15, 1982

[51] Int. Cl.$^3$ ............................................. B29C 13/00
[52] U.S. Cl. .................................. 264/303; 264/301; 264/304; 264/306; 264/307; 264/DIG. 51
[58] Field of Search ............... 264/301, 304, 306, 307, 264/DIG. 51, 303

[56] References Cited

U.S. PATENT DOCUMENTS

| | | | |
|---|---|---|---|
| 2,621,166 | 12/1952 | Schmidt et al. | 525/440 |
| 2,625,535 | 1/1953 | Mastin et al. | 528/74 |
| 2,770,612 | 11/1956 | Schollenberger | 525/440 |
| 2,899,411 | 8/1959 | Schollenberger | 528/76 |
| 2,968,575 | 1/1961 | Mallonee | 524/839 |
| 2,998,403 | 8/1961 | Müller et al. | 528/76 |
| 3,002,231 | 10/1961 | Walker et al. | 264/DIG. 51 |
| 3,148,235 | 9/1964 | Velonis et al. | 264/301 |
| 3,553,308 | 1/1971 | Suita et al. | 264/307 |
| 3,591,561 | 7/1971 | Kazama et al. | 528/59 |
| 3,684,770 | 8/1972 | Meisert et al. | 528/65 |
| 3,689,443 | 9/1972 | Fensch | 525/441 |
| 3,804,812 | 4/1974 | Koroscil | 528/65 |
| 3,846,378 | 11/1974 | Griswold | 428/365 |
| 3,857,818 | 12/1974 | Frizelle | 525/124 |
| 3,917,741 | 11/1975 | McGarr | 528/48 |
| 3,927,161 | 12/1975 | Powell | 264/DIG. 51 |
| 4,131,604 | 12/1978 | Szycher | 528/79 |
| 4,252,923 | 2/1981 | König et al. | 425/452 |
| 4,284,745 | 8/1981 | Meyer et al. | 525/408 |

OTHER PUBLICATIONS

Polymers in Medicine & Surgery, Kronenthal, et al., Plenum. Press, vol. 8, p. 45 etc.

*Primary Examiner*—James H. Derrington
*Attorney, Agent, or Firm*—Biebel, French & Nauman

[57] ABSTRACT

A powder coating process for producing soft, flexible polyurethane films particularly in the form of a surgical glove, wherein low melting crystalline prepolymer particles are powder coated and cured to an essentially non-crystalline film.

20 Claims, No Drawings

POWDER COATING PROCESS FOR FORMING SOFT FLEXIBLE POLYURETHANE FILM

BACKGROUND OF THE INVENTION

The present invention relates to a process for forming a soft, flexible polyurethane film by powder coating and, more particularly, to a process for forming a low modulus essentially non-crystalline polyurethane film which is free of pin holes.

Although powder coating techniques have been used to coat some polyurethane varnishes to form hard, brittle, inelastic coatings, they have not been used to form soft, flexible self sustaining films. One reason they probably have not been used to form flexible polyurethane films is that such films are essentially non-crystalline and under conventional thinking would be prepared from non-crystalline prepolymers which would not be grindable to a powder.

Soft, flexible polyurethane films have been formed by solution coating. One of the problems that is encountered when forming soft polyurethane films from solution is that as the thickness of the film increases, solvent bubbles form and cause pin holes in the film as the solvent evaporates. This makes it difficult to use polyurethanes in applications where a pin hole free film is required, as in the case of manufacturing surgical gloves, prophylactics, catheter balloons, etc.

A pin hole free polyurethane film has been obtained in a two-coat process wherein first a very thin primer film of polyurethane prepolymer is coated from solution and cured, followed by powder coating to build up the film thickness. The primer film providing a base upon which particles of polyurethane prepolymer can flow out into a continuous film. Thus, the process has the effect of forming two films which prevent pinholes from extending from one face of the film to another. The process, however, suffers the inefficiencies in providing two different and independent coating solutions, separate cures after the first and second coats, and two prepolymer supplies, one a solution and the other a powder. Hence, there is a need for a more efficient process for producing pin hole free polyurethane films, and, particularly, a process that can be performed at one coating station.

SUMMARY OF THE INVENTION

Thus, it is an object of the present invention to provide an all powder coating process for producing a soft, flexible essentially non-crystalline polyurethane film.

It is a more particular object of the invention process to provide an all powder coating process for producing a polyurethane film in the form of a surgical glove.

One of the problems encountered when attempting to powder coat a polyurethane prepolymer is that the prepolymer particles do not flow out and meld into the continuous film as is necessary to obtain a pin hole free film. Rather, due to the viscosity of the wetted prepolymer or the surface tension of the powder droplets that form or both, complete coalescence is not obtained throughout the coated film and voids remain. In the two coat process described above, this is overcome by priming the film form with a layer of the prepolymer on which the prepolymer particles readily flow out and meld. Leaks are prevent by a two film effect that is achieved. In the present invention the powder coated particles melt and flow out into a continuous film without the need of a primer coating. This is accomplished using a combination of techniques including the use of prepolymers having enhanced flow characteristics, better fluidization of the prepolymer powder through cooling, pre-heating the film former, and controlled curing. Thus, a thin continuous essentially pin hole free polyurethane film is achieved by powder coating.

Thus, one embodiment the present invention provides a process for forming a soft, flexible polyurethane film which comprises fluidizing finely divided particles of a polyurethane prepolymer having a crystalline melt point in the range of approximately 10° to 45° C., pre-heating a film form to a temperature at which the prepolymer particles will adhere to the form upon contact with it, immersiing the pre-heated form in the fluidized particles such that the particles deposit on the form, the particles thereby flowing out into a thin continuous pin hole free film.

Another, more specific embodiment of the invention is an all powder coating process for forming surgical gloves and similar gloves of a flexible nature. In accordance with this process films are formed in the manner described above on a glove form. In a preferred embodiment, in pre-heating the glove form to adhere the powder, a temperature profile is used in which certain portions of the glove form are heated to higher temperatures than others to compensate for temperature differences in the fluidized bed and to make certain portions of the glove, such as the cuff, thicker than others.

DEFINITIONS

The terms defined below are used in describing prepolymers useful in the invention process.

Tear is Die C tear and measured in accordance with ASTM D624.

Tensile, modulus and elongation are measured in accordance ASTM D412-68.

Initial tensile set as used herein is the percent set as determined immediately after testing elongation in accordance with ASTM D412-68 by measuring the percent increase between 1 inch markings without allowing time for recovery.

Molecular weight per cross-link ($M_c$) is calculated as set forth in POLYURETHANES CHEMISTRY AND TECHNOLOGY, Saunders and Frisch, Robert E. Krieger Publishing Co., Huntington, N.Y. (1978) p. 266.

DETAILED DESCRIPTION OF THE INVENTION

In accordance with the present invention, essentially pin hole free flexible polyurethane films and more specifically flexible gloves are formed by powder coating.

The invention process is useful in forming thermosetting or thermoplastic flexible polyurethane films. When used in forming surgical gloves, the process is preferably used to form thermosetting films using low melting crystalline pre-polymers.

In order to powder coat a soft, flexible polyurethane film, the polymer or prepolymer thereof must be sufficiently brittle to be grindable into powder form but, at the same time, form a film which is soft and flexible. While the invention has application to coating with both polyurethane polymer and prepolymers, it is described below by reference to the coating of prepolymers.

In the case of coating polyurethane prepolymers to obtain a low modulus polyurethane film, this equates to a requirement of a crystalline grindable prepolymer which is polymerizable to a soft essentially non-crystalline film. Furthermore, the prepolymer must have such flow characteristics that it flows out into a thin continuous film without forming pin holes.

Various prepolymers can be coated in accordance with the present invention. Those prepolymers that are most useful in obtaining a flexible, essentially non-crystalline films have a crystalline melt point in the range of about 10° to 45° C. and, more preferably 20° to 40° C. They are available by pre-reacting a long chain diol having a molecular weight of about 500 to 5000, an organic polyisocyanate and, depending on the properties desired in the polymer, an extender and a cross-linking agent. Preferred prepolymers are end-blocked and more particularly end-blocked with a heat-reversible end blocking agent.

The long chain diols used in the present invention may be polyester diols or polyether diols. Typically the diols range from approximately 500 to 5000 and preferably 1000 to 3000 in molecular weight and have a crystalline melt point of about 25° to 70° C. Representative examples are polylactone diols such as polycaprolactone diol and copolymers of short chain diols (e.g., primary diols having 2 to 4 carbon atoms) and aliphatic dicarboxylic acids (e.g., having 4 to 10 carbon atoms) such as poly(ethylene adipate) diol, poly(ethylene succinate) diol, poly(ethylene sebacate) diol, poly(butylene adipate) diol, etc.

In some cases it is advantageous to use a mixture of long chain diols to obtain an essentially non-crystalline film through melting point depression. Thus, a mixture of two or more diols can be used to prepare the prepolymer powder used in the invention. The mixture can be a mixture of one diol in different molecular weights, but the effect is more pronounced where two chemically different diols are used. Hence, in one embodiment of the invention, a diol mixture such as polycaprolactone diol and poly(ethylene adipate) diol may be used to prepare the prepolymer. A mixture of diols having melting points outside the aforementioned range can also be used in the present invention if the fully cured film is essentially non-crystalline.

An extender and/or a cross-linking agent may be reacted in forming the prepolymer. When a thermosetting film is desired, as in the case of making surgical gloves, a cross-linking agent is reacted in the prepolymer. The present invention is not limited to a particular cross-linking agent or extender as the compounds selected will depend on the film characteristics that are desired. For illustration, however, one class of extenders that is particularly convenient because they are readily mixed with the long chain diol in forming the prepolymer are short chain diols having 2 to 6 carbon atoms in the main chain such as ethylene glycol, propylene glycol, 1,4 butanediol, neopentyl glycol, etc. In addition, alicyclic diols such as cyclohexanediol, and 1,4 dimethylol cyclohexane can be used. Another common polyurethane extender is a diamine such as ethylenediamine.

Polyhydroxy compounds, typically having at least 3 hydroxyl groups, are useful and convenient cross-linking agents. Very often an adduct of a long chain diol and a short chain polyol (e.g., trimethylolpropane, trimethyolethane, etc.), is used such as Union Carbide PCP 0300 which is an adduct of ε-caprolactone and trimethyolpropane having a molecular weight of about 540. Otherwise, the short chain polyols themselves can be used as cross-linking agents. The amount of cross-linking agent is adjusted to provide an essentially non-crystalline polymer and to provide the other film properties that may be desired.

For surgical gloves, where the polymer film must have low set and low modulus, the amount of cross-linking agent is adjusted to provide a degree of cross-linking (Mc) of about 5,000 to 30,000, preferably 8,000 to 25,000. These films are characterized by 100% modulus less than 250 psi. By controlling the degree of cross-linking and the molecular weight of the long chain diol, films having a 300% modulus of about 200 to 500 psi, elongation at break greater than 600 psi, and tear greater than 100 ppi are obtained. Generally the prepolymers used in making surgical gloves by the invention process are obtained by reacting approximately: 13 to 23% polyisocyanate (all percents are by weight exclusive of the end-blocking agent unless otherwise indicated), 0.75 to 6% polyhydroxy cross-linking agent, up to 3% extender, and the balance long chain polyol; the end blocking agent being used in an amount equivalent to approximately 5 to 30% of the isocyanate groups in the polyisocyanate.

Prepolymers which are end-blocked using a heat reversible end blocking agent are desirable in the present invention because they can be cured to the full polymer without the use of chemical reagents. Preferred as end-blocking agents are those which can be removed at temperatures, less than 200° C. Particularly preferred end-blocking agents are oximes such as acetone oxime and methyl ethyl ketone oxime. The oximes are also advantageous because they make it possible to synthesize the prepolymers in a one shot synthesis wherein the oxime is added to the long chain diol together with any extender and cross-linking agents (which are also preferably hydroxy compounds). The oxime may also be pre-reacted with the polyisocyanate.

Any of the organic polyisocyanate conventionally used in polyurethanes can be used in preparing the prepolymers coated in accordance with this invention. This selection will depend both on the properties that are desired in the polymer film and on their effect on the prepolymer as discussed above. In the manufacture of surgical gloves, alicyclic and aromatic polyisocyanates and, more specifically, diisocyanates are preferred although linear aliphatic diisocyanates could also be used. Representative polyisocyanates for use in the present invention include 4,4' diphenyl methane diisocyanates (MDI) methylene bis (4-cyclohexyl isocyanate) (HMDI), toluene diisocyanate (TDI), isophorone diisocyanate (IPDI), etc. Tetraisocyanates and triisocyanates can also be used.

Prepolymers having melt point below or in the vicinity of room temperature are not grindable and they cannot be fluidized at room temperature, however, these prepolymers are often the most advantageous because they yield a very soft and flexible polyurethane films. In a preferred embodiment of the present invention polyurethane prepolymer powders prepared from one of the aforementioned low melting crystalline prepolymers are used. These prepolymers are ground by cooling them to temperatures below their crystalline melt point. After they are ground they are refrigerated. Powder coating is conducted by fluidizing the ground powder while the bed is cooled to a temperature below the crystalline melt point of the powder. The bed is typically cooled to a temperature of about 5° to 40° C. below the melt point of the particles. It has been found that cooling the bed improves fluidization by hardening the powder particles and reducing their tack. This makes the bed more uniform and provides better coating control. In fact, it is also desirable to cool the bed when using powders having crystalline melt points above room temperature to reduce tack and improve fluidization.

The powder used in the present invention may range in particle size from about 1 to 100 microns, preferably with at least 80% by weight of the particles in the range of 20 to 75 microns. Particles larger than 100 microns tend to agglomerate as they melt out on the film form and leave voids in the film.

To powder coat the film form, the form is pre-heated to a temperature at which the polymer particles will deposit on the form from a fluidized bed. As a general rule the form is heated to a temperature about 10° to 100° C. higher than the crystalline melt point of the prepolymer. The temperature of the form determines whether the powder simply attaches to the form or melts out into a continuous film. If the form is only 10° to 20° C. higher than the melting point of the prepolymer, the powder will attach to the form without melting out into a film. To produce a film directly, the temperature of the form should be at least 50° C. higher than the crystalline melt point of the prepolymer. Both practices can be used in the present invention although the latter is generally more desirable. When the powder only attaches to the form, it must be melted out by additional heating prior to curing.

The invention process can be used to form films of 3.5 mils and greater thickness and preferably of 4.5 mils and greater thickness. Film thickness is a function the temperature of the form and the time the form is immersed in the fluidized bed. Higher form temperatures quickly melt or soften the coated particles and provide greater film thickness. Using the preferred low melting prepolymers the form is pre-heated to approximately 90° to 150° C. for coating. To illustrate the effect of immersion time on film thickness, to form a film 5.0 mils thick, a form pre-heated to 105° C. may be immersed in a fluidized bed of polyurethane prepolymer 1.5 seconds. By comparison, to form a film 6.0 mils thick, a form pre-heated to 105° C. may be immersed in a fluidized bed 2 seconds.

In a preferred embodiment of the invention, surgical glove forms are heated differentially to impart a temperature profile to the form whereby the powder pick up can be controlled. By pre-heating certain portions of a glove form to higher temperatures, the film thickness can be increased or coating variations due to differences in immersion time and bed temperature can be compensated. For example, it is desirable to make the cuff thicker than the balance of the glove since the cuff is used to pull the glove onto the hand. Thus, using one of the preferred prepolymers described above, the cuff portions of the form are heated to 125° C. whereas the palm and finger portions are heated to about 100° C. Differential heating is also useful to compensate for differences in immersion time when dipping a form into and out of a bed where the first portions to enter the bed are also the last to leave and therefor have the opportunity accumulate more polymer. As an illustration, when making surgical gloves by dipping the fingers first, the fingers are pre-heated to a lower temperature since they are first to enter and last to leave the fluidized bed.

After coating, the form is withdrawn from the bed and the applied melted powder is further heated and cured. While heating can be carried out at one temperature it is generally desirable to heat the film in two stages, first at a lower temperature without curing to eliminate microbubbles and then at a higher temperature to cure the films. The temperatures will depend on the prepolymer that is used. Using a preferred acetone oxime end blocked prepolymer, suitable first stage temperatures range from about 90° to 140° C. and suitable cure temperatures range from about 130° to 180° C.

Due to the high adhesion of polyurethanes, it is necessary to pre-treat the film form with a release agent prior to powder coating. Conventional mold release agents such as silicone compounds and poly(tetrafluoroethylene) may be used. Furthermore, it is also desirable to incorporate a mold release assistant into the polyurethane itself. One that can be used is a silicon diol such as Dow Corning Q4-3667 which is co-polymerized into the polymer with the long chain diol.

Films formed in the present invention can be pigmented by simply mixing pigment with the prepolymer powder. Typically the pigment is admixed with the powder in amounts up to 2% by weight or as required. In forming surgical gloves umber and $TiO_2$ are most often used. It has been found that the presence of pigment in the bed improves fluidization. Finely divided silica is usually also added to the bed as an a fluidizing assistant.

Prepolymers synthesized prepared according to the following examples are useful in the present invention.

EXAMPLE 1

A polyurethane prepolymer was prepared by mixing 10 grams of a 540 MW polycaprolactone triol (Union Carbide PCP-0300), 117 g of a 1250 MW polycaprolactone diol (Union Carbide PCP-0230), 153 g of a 2,000 MW polycaprolactone diol (Union Carbide PCP-0240), 23 g of Dow Corning Q4-3667 (a long chain silicon diol), 9 g of 1,4 butanediol and 6 g of acetone oxime in a suitable reactor and heating the mixture to 50° C. To this mixture was added 82 g of molten 4,4′ diphenyl methane diisocyanate and 0.12 g of dibutyl tin dilaurate (M+T chemical, T-12). A crystalline grindable polyurethane prepolymer was obtained which when reacted, provided the properties set forth in Table I below. Unless otherwise indicated, all percents are by weight.

TABLE I

| Hard Segment % | 22.7 |
| --- | --- |
| $M_c$ | 16,000 |
| Long Chain Diol % | 73 |
| Cross-linking agent % | 2.5 |
| Isocyanate % | 20.8 |
| Tensile (psi) | 5,500 |
| Modulus Youngs (psi) | 390 |
| 100% (psi) | 140 |
| 300% (psi) | — |
| Elongation % | 605 |
| Tear (ppi) | 115 |
| Set % | 13 |

EXAMPLE 2

Using the same procedure as Example 1, a polyurethane prepolymer was prepared by mixing 8 g of 540 MW polycaprolactone triol (PCP-0300), 319 g of 2000 MW poly(ethylene-butylene) adipate glycol 7 g of 1,4 butanediol and 5 g of acetone oxime, and adding to the heated mixture 66 g 4,4′ diphenyl methane diisocyanate with 0.12 g dibutyl tin dilaurate. The polyurethane obtained upon heating this prepolymer has the properties shown in Table II.

TABLE II

| | |
|---|---|
| Hard Segment (%) | 18 |
| $M_c$ | 19,400 |
| Long Chain diol (%) | 79.7 |
| Crosslinking agent (%) | 2.1 |
| Isocyanate content, (%) | 16.6 |
| Tensile psi | 3500 |
| Modulus | 310 |
| Youngs, psi | |
| 100%, psi | 190 |
| 300%, psi | 280 |
| Elongation (%) | 760 |
| Tear (ppi) | 110 |
| Set (%) | 11 |

EXAMPLES 3 AND 4

Polyurethane prepolymers were prepared from the reactants set forth in Table III below by the procedure set forth in Example 1. The polyurethanes obtained upon reacting these prepolymers have the composition and physical properties shown in Table III.

TABLE III

| | Ex. 3 | Ex. 4 |
|---|---|---|
| 540 M.W. Polycaprolactone Triol (PCP 0300) | 9 g | 13 g |
| 2000 M.W. Poly(ethylene adipate) glycol | 279 g | 237 g |
| 1000 M.W. Poly(ethylene adipate) glycol | 0 g | 30 g |
| Dow Corning Q4-3667 | 24 g | 28 g |
| 1,4 Butanediol | 10 g | 9 g |
| 4,4' diphenyl methane diisocyanate | 73 g | 77 g |
| Acetone Oxime | 6 g | 6 g |
| Dibutyl Tin Dilaurate | 0.12 g | 0.12 g |
| Hard Segment (%) | 20.7 | 21.5 |
| $M_c$ | 17,300 | 13,200 |
| Long chain diol (%) | 75.6 | 73.8 |
| Crosslinking agent, (%) | 2.3 | 3.2 |
| Isocyanate content, (%) | 18 | 19 |
| 2 Months Physicals | | |
| Tensile (psi) | 6600 | 3800 |
| Modulus | 420 | 320 |
| Youngs (psi) | | |
| 100% (psi) | 170 | 130 |
| 300% (psi) | 350 | 240 |
| 500% (psi) | 1300 | 650 |
| Elongation (%) | 750 | 690 |
| Tear (ppi) | 140 | 105 |
| Set (0/6) | 11 | 10 |

EXAMPLE 5

Using the same procedure set forth in Example 1, a polyurethane prepolymer was prepared by mixing 11.3 grams of a 540 MW polycaprolactone triol, 128.5 grams of a 3000 MW poly(ethylene, 1,4-butane adipate) diol, 158.9 grams of a 2000 MW poly(ethylene adipate) diol, (Witco Chemical, Formrez 22-56), 17.96 grams Dow Corning Q4-3667, 8.7 grams of 1,4-butanediol and 5.2 grams of acetone oxime and adding to the heated mixture 69.5 grams of HMDI and 0.12 grams dibutyl tin dilaurate to prepare a prepolymer. The prepolymer obtained was granular and crystalline and was fused into a continuous film and cured as in Example 1. The polyurethane obtained had the properties shown in Table IV.

TABLE IV

| | |
|---|---|
| Hard Segment (%) | 19.8 |
| Mc | 11,106 |
| Long Chain Diol (%) | 77.3 |
| Cross-Linking Agent (%) | 2.9 |
| Isocyanate (%) | 17.6 |
| Acetone oxime (eq. %) | 13.4 |
| Tensile (psi) | 5236 |
| Modulus | 384 |
| Young's (psi) | |
| 100% (psi) | 207 |
| 300% (psi) | 482 |
| Elongation (%) | 843 |
| Tear ppi | 284 |
| Set % | 12 |

EXAMPLE 6

Using the same procedure set forth in Example 1, a prepolymer was prepared by mixing 12.8 grams of a 540 MW polycaprolactone triol, 230.23 grams of a 2000 MW poly(ethylene adipate) diol, 39.3 grams of a 1000 MW poly(ethylene adipate) diol (Hooker Chemical, Rucoflex 5101-110), 21.05 Dow Corning Q4-3667, 9.1 grams of 1,4-butanediol and 6.2 g acetone oxime, and adding to the heated mixture 81.4 grams of methylene bis (4-cycholexyl isocyanate) and 0.12 grams of dibutyl tin dilaurate. A crystalline, grindable prepolymer was obtained which fused into a film and was cured as in Example 1. The polyurethane obtained had the properties shown in Table V.

TABLE IV

| | |
|---|---|
| Hard Segment % | 23.0 |
| Mc | 9,476 |
| Long Chain Diol (%) | 73.8 |
| Crosslinking Agent (%) | 3.2 |
| Isocyanate (%) | 20.7 |
| Acetone Oxime (eq %) | 13.4 |
| Tensile (psi) | 4782 |
| Modulus | 412 |
| Young's (ppi) | |
| 100% (psi) | 207 |
| 300% (psi) | 497 |
| Elongation (%) | 755 |
| Tear (ppi) | 210 |
| Set, (%) | 23 |

EXAMPLE 7

A polyurethane prepolymer was obtained by preparing a diol mixture containing 22 parts of a 540 MW polycaprolactone triol (Union Carbide PCP-0300), 703 parts of 2000 MW poly(ethylene adipate) glycol (Formrez 24-56, Witco Chemical Co.), 24 parts of 1,4 butanediol, and 58 parts of Dow Corning Q4-3667 silicone diol, as a release assistant, 14 parts of acetone oxime and 0.3 parts of dibutyl tin dilaurate. The diol mixture was heated to 50° C. and 179 parts of 4,4' diphenyl methane diisocyanate were added thereto at a mixing head which heated to 90° C. under the reaction exotherm. The reaction product was poured into a pan to form a solid slab and allowed to stand 3 days at room temperature. Prepolymer prepared as above was crystalline and grindable.

The invention is illustrated in more detail by the following non-limiting example of a glove forming process in accordance with the present invention. While the invention process is illustrated using one particular prepolymer powder, it will be evident that with the appropriate modifications any of the prepolymers illustrated above could be used to form gloves by powder coating in accordance with this invention.

EXAMPLE 8

The surfaces of porcelain gloves forms were pre-treated with Dow Corning 360 Medical fluid for release properties.

Polyurethane prepolymer powder was obtained by preparing a mixture of 255 parts poly(ethylene-adipate) diol (Formerez 22-56), 9 parts Union Carbide PCP 0300, 10 parts 1,4 butanediol, 24 parts Dow Corning Q-3446 and 6 parts acetone oxime. To this mixture was added 73 parts 4,4' diphenyl methane diisocyanate and 0.024% dibutyl tin dilaurate. The mixture was heated to about 50° C. and the reaction exotherm carried the temperature to about 90° C. such that the product could be poured out into a slab, where it was allowed to stand 3 days. The prepolymers obtain exhibited a crystalline melt point of about 35° to 45° C.

Prepolymer obtained as above was cooled with liquid nitrogen and ground using an attrition grinder to a weight average particle size of 50 microns.

The powder was refrigerated until use, wereupon it was fluidized with dry nitrogen at a temperature of about 5° C. The bed concentration was about 26 lbs/ft³.

A glove form prepared as above was heated to 105° C. in the palm, 100° C. in the fingers, and 135° C. in the cuff and immersed, fingers first, into the bed. The form remained in the bed approximately 1.6 seconds whereupon a powder layer about 5.5 mils thick was built up on the glove form. Thereafter, the form was transported through an oven heated to about 140° C. for 8 min. and then to an oven heated to about 155° C. where it remained about 6 min to drive off the oxime and produce the fully cured polymer.

A glove which was essentially pin hole free having a thickness of 5.5 mils in the palm was obtained.

Having described my invention in detail and by reference to specific embodiments thereof, it will be apparent that numerous modifications and variations are possible without departing from the spirit and scope of the following claims.

What is claimed is:

1. A process for forming a soft, flexible polyurethane film which consists essentially of:
   (a) fluidizing finely divided particles of a polyurethane prepolymer, said prepolymer having a crystalline melt point in the range of approximately 10° to 45° C.,
   (b) pre-heating a film form to a temperature at which said particles will adhere to said form when in contact therewith,
   (c) immersing said pre-heated form into said fluidized particles such that said particles deposit on said form,
   (d) heating said form to melt said particles such that said particles flow out into a thin, continuous, essentially pin hole free film, and
   (e) removing said film from said form;
   wherein said prepolymer comprises the reaction product of an organic polyisocyanate, a crystalline long chain diol having an average molecular weight of approximately 500 to 5000, a polyhydroxy crosslinking agent and an end blocking agent, wherein the resulting polyurethane elastomer has a 100% modulus less than approximately 250 psi and a 300% modulus between 200 and 500 psi.

2. The process of claim 1 wherein said film form is pre-treated with a release agent.

3. The process of claim 2 wherein at least 80% by weight of said particles range from about 20 to 75 microns in size.

4. The process of claim 1 wherein said process additionally comprises curing said film.

5. The process of claim 1 wherein certain portions of said form are pre-heated to higher temperatures than other portions.

6. The process of claim 1 wherein said particles are cooled as they are fluidized.

7. A process for forming a surgical glove and similar gloves of a flexible nature which consists essentially of:
   (a) fluidizing finely divided particles of a polyurethane prepolymer, said prepolymer having a crystalline melt point in the range of approximately 10° to 45° C.,
   (b) pre-heating a film form to a temperature at which said particles will adhere to said form when in contact therewith,
   (c) immersing said pre-heated form into said fluidized particles such that said particles deposit on said form,
   (d) heating said form to melt said particles such that said particles flow out into a thin, continuous, essentially pin hole free film, and
   (e) removing said film from said form to provide said glove;
   wherein said prepolymer comprises the reaction product of an organic polyisocyanate, a crystalline long chain diol having an average molecular weight of approximately 500 to 5000, a polyhydroxy crosslinking agent and an end blocking agent, wherein the resulting polyurethane elastomer has a 100% modulus less than approximately 250 psi and a 300% modulus between 200 and 500 psi.

8. The process of claim 7 wherein said glove form is pre-treated with a release agent.

9. The process of claim 8 wherein at least 80% by weight of said particles range from about 20 to 75 microns in size.

10. The process of claim 9 wherein said glove form has the cuff portion preheated to a higher temperature than the finger portion.

11. The process of claim 7 wherein said particles are cooled as they are fluidized.

12. The process of claim 7 wherein said process additionally comprises curing said film.

13. A process for forming a surgical glove and similar gloves of a flexible nature which consists essentially of:
   (a) fluidizing finely divided particles of a polyurethane prepolymer,
   (b) pre-heating a glove form to a temperature at which said particles will adhere to said form when in contact therewith,
   (c) immersing said pre-heating form into said fluidized particles such that said particles deposit on said form,
   (d) heating said form to melt said particles such that said particles flow out into a thin, continuous, essentially pin hole free film;
   (e) curing said film, and
   (f) removing said film from said form to provide said glove;
   wherein said prepolymer comprises the reaction product of an organic polyisocyanate, a crystalline long chain diol having an average molecular weight of approximatly 500 to 5000, a polyhydroxy crosslinking agent and an end blocking agent, wherein the resulting polyurethane elastomer has a 100% modulus less than approximately 250 psi and a 300% modulus between 200 and 500 psi.

14. The process of claim 1 wherein:
   (a) said organic polyisocyanate is selected from the group consisting of 4,4'-diphenylmethane diisocyanate, toluene diisocyanate, isophorone diisocyanate, and methylene bis (4-cyclohexyl isocyanate), and
   (b) said crystalline long chain diol has a molecular weight of 1000 to 5000 and is selected from the group consisting of polycaprolactone glycol, poly(ethylene adipate) glycol, poly(ethylene succinate) glycol, poly(ethylene sebacate) glycol, poly(butylene adipate) glycol and mixtures thereof.

15. The process of claim 7 wherein:
   (a) said organic polyisocyanate is selected from the group consisting of 4,4'-diphenylmethane diisocyanate, toluene diisocyanate, isophorone diisocyanate, and methylene bis (4-cyclohexyl isocyanate), and
   (b) said crystalline long chain diol has a molecular weight of 1000 to 5000 and is selected from the group consisting of polycaprolactone glycol, poly(ethylene adipate) glycol, poly(ethylene succinate) glycol, poly(ethylene sebacate) glycol, poly(butylene adipate) glycol and mixtures thereof.

16. The process of claim 13 wherein:
   (a) said organic polyisocyanate is selected from the group consisting of 4,4'-diphenylmethane diisocyanate, toluene diisocyanate, isophorone dissocyanate, and methylene bis (4-cyclohexyl isocyanate), and
   (b) said crystalline long chain diol has a molecular weight of 1000 to 5000 and is selected from the group consisting of polycaprolactone glycol, poly(ethylene adipate) glycol, poly(ethylene succinate) glycol, poly(ethylene sebacate) glycol, poly(butylene adipate) glycol and mixtures thereof.

17. The process of claim 1 wherein said prepolymer comprises the reaction product of:
   (a) about 13 to 23% by weight of an organic polyisocyanate selected from the group consisting of 4,4'-diphenylmethane diisocyanate, toluene diisocyanate, isophorone diisocyanate, and methylene bis (4-cyclohexyl isocyanate),
   (b) about 70 to 84% by weight of a crystalline long chain diol having a molecular weight of 1000 to 5000 and a melting point of 30° to 55° C. selected from the group consisting of polycaprolactone glycol, poly(ethylene adipate) glycol, poly(ethylene succinate) glycol, poly(ethylene sebacate) glycol, poly(butylene adipate) glycol and mixtures thereof,
   (c) a polyhydroxy crosslinking agent in an amount sufficient to provide a crosslinking degree in the range of approximately 5000 to 30,000 $M_c$,
   (d) up to about 3% of a short chain diol extender, and
   (e) an end-blocking agent in an amount sufficient to block about 5 to 30% of the isocyanate groups forming said polyisocyanate.

18. The process of claim 7 wherein said prepolymer comprises the reaction product of:
   (a) about 13 to 23% by weight of an organic polyisocyanate selected from the group consisting of 4,4'-diphenylmethane diisocyanate, toluene diisocyanate, isophorone diisocyanate, and methylene bis (4-cyclohexyl isocyanate),
   (b) about 70 to 84% by weight of a crystalline long chain diol having a molecular weight of 1000 to 5000 and a melting point of 30° to 55° C. selected from the group consisting of polycaprolactone glycol, poly(ethylene adipate) glycol, poly(ethylene succinate) glycol, poly(butylene adipate) glycol and mixtures thereof,
   (c) a polyhydroxy crosslinking agent in an amount sufficient to provide a crosslinking degree in the range of approximately 5000 to 30,000 $M_c$,
   (d) up to about 3% of a short chain diol extender, and
   (e) an end-blocking agent in an amount sufficient to block about 5 to 30% of the isocyanate groups forming said polyisocyanate.

19. The process of claim 13 wherein said prepolymer comprises the reaction product of:
   (a) about 13 to 23% by weight of an organic polyisocyanate selected from the group consisting of 4,4'-diphenylmethane diisocyanate, toluene diisocyanate, isophorone diisocyanate, and methylene bis (4-cyclohexyl isocyanate),
   (b) about 70 to 84% by weight of a crystalline long chain diol having a molecular weight of 1000 to 5000 and a melting point of 30° to 55° C. selected from the group consisting of polycaprolactone glycol, poly(ethylene adipate) glycol, poly(ethylene succinate) glycol, poly(ethylene sebacate) glycol, poly(butylene adipate) glycol and mixtures thereof,
   (c) a polyhydroxy crosslinking agent in an amount sufficient to provide a crosslinking degree in the range of approximately 5000 to 30,000 $M_c$,
   (d) up to about 3% of a short chain diol extender, and
   (e) an end-blocking agent in an amount sufficient to block about 5 to 30% of the isocyanate groups forming said polyisocyanate.

20. The process of claim 13 wherein said polyurethane prepolymer has a crystalline melt point in the range of about 10° to 45° C.

* * * * *